(12) United States Patent
Treado et al.

(10) Patent No.: US 9,103,714 B2
(45) Date of Patent: *Aug. 11, 2015

(54) SYSTEM AND METHODS FOR EXPLOSIVES DETECTION USING SWIR

(75) Inventors: Patrick Treado, Pittsburgh, PA (US); Matthew Nelson, Harrison City, PA (US); Charles W. Gardner, Jr., Gibsonia, PA (US)

(73) Assignee: ChemImage Corporation, Pittsburgh, PA (US)

( * ) Notice: Subject to any disclaimer, the term of this patent is extended or adjusted under 35 U.S.C. 154(b) by 579 days.

This patent is subject to a terminal disclaimer.

(21) Appl. No.: 12/924,831

(22) Filed: Oct. 6, 2010

(65) Prior Publication Data

US 2011/0089323 A1 Apr. 21, 2011

Related U.S. Application Data

(63) Continuation-in-part of application No. 12/754,229, filed on Apr. 5, 2010.

(60) Provisional application No. 61/335,785, filed on Jan. 12, 2010, provisional application No. 61/278,393, (Continued)

(51) Int. Cl.
  *G01J 3/02* (2006.01)
  *G01J 3/44* (2006.01)
  (Continued)

(52) U.S. Cl.
  CPC .. *G01J 3/02* (2013.01); *G01J 3/027* (2013.01); *G01J 3/0218* (2013.01); *G01J 3/0278* (2013.01); *G01J 3/44* (2013.01); *G01N 21/359* (2013.01); *G01N 33/0057* (2013.01)

(58) Field of Classification Search
  CPC .... G01J 3/02; G01J 3/2823; G01J 2003/2826
  USPC ...................... 356/72–73; 250/334
  See application file for complete search history.

(56) References Cited

U.S. PATENT DOCUMENTS

| | | | |
|---|---|---|---|
| 3,679,307 A | 7/1972 | Zoot |
| 4,711,577 A | 12/1987 | Hull-Allen |
| 4,952,816 A | 8/1990 | Dunning |

(Continued)

FOREIGN PATENT DOCUMENTS

| | | |
|---|---|---|
| EP | 2083259 | 7/2009 |
| WO | PCT/US05/25112 | 2/2006 |

(Continued)

OTHER PUBLICATIONS

Onat, Bora M. et al., A Solid State Hyperspectral Imager for Real-Time Standoff Explosives Detection Using Shortwave Infrared Imaging, Proc. of SPIE vol. 7310, 731004-1 to 731004-11, 2009.

(Continued)

*Primary Examiner* — Kara E Geisel
(74) *Attorney, Agent, or Firm* — Pepper Hamilton LLP

(57) ABSTRACT

A system and method for detecting explosives and explosive residues. A region of interest is surveyed using a video capture device to thereby identify a target area wherein the target area comprises an unknown material. The target area is interrogated using SWIR spectroscopic methods to form a SWIR hyperspectral image of the target area. The SWIR hyperspectral image is analyzed to thereby identify the unknown material.

16 Claims, 17 Drawing Sheets
(9 of 17 Drawing Sheet(s) Filed in Color)

Related U.S. Application Data filed on Oct. 6, 2009, provisional application No. 61/301,814, filed on Feb. 5, 2010, provisional application No. 61/305,667, filed on Feb. 18, 2010, provisional application No. 61/403,141, filed on Sep. 10, 2010, provisional application No. 61/324,963, filed on Apr. 16, 2010.

(51) Int. Cl.
  *G01N 21/359* (2014.01)
  *G01N 33/00* (2006.01)

(56) References Cited

U.S. PATENT DOCUMENTS

| | | | |
|---|---|---|---|
| 5,216,484 A * | 6/1993 | Chao et al. | 356/326 |
| 5,528,368 A | 6/1996 | Lewis | |
| 5,602,394 A * | 2/1997 | Dombrowski et al. | 250/339.02 |
| 5,606,164 A | 2/1997 | Price et al. | |
| 6,008,492 A | 12/1999 | Slater | |
| 6,075,891 A | 6/2000 | Burman | |
| 6,208,749 B1 | 3/2001 | Gutkowicz | |
| 6,244,535 B1 | 6/2001 | Felix | |
| 6,274,871 B1 | 8/2001 | Dukor | |
| 6,421,553 B1 | 7/2002 | Costa et al. | |
| 6,422,508 B1 | 7/2002 | Barnes | |
| 6,658,915 B2 | 12/2003 | Sunshine | |
| 6,717,668 B2 | 4/2004 | Treado | |
| 6,826,358 B2 | 11/2004 | Partunski | |
| 6,967,612 B1 | 11/2005 | Gorman | |
| 6,985,216 B2 | 1/2006 | Treado et al. | |
| 6,992,809 B1 | 1/2006 | Wang | |
| 7,012,695 B2 | 3/2006 | Maier et al. | |
| 7,019,296 B2 | 3/2006 | Treado et al. | |
| 7,061,606 B2 | 6/2006 | Treado et al. | |
| 7,068,357 B2 | 6/2006 | Treado et al. | |
| 7,072,770 B1 | 7/2006 | Schweitzer et al. | |
| 7,088,435 B2 | 8/2006 | Brestel | |
| 7,123,360 B2 | 10/2006 | Treado et al. | |
| 7,194,111 B1 | 3/2007 | Schaum | |
| 7,239,974 B2 | 7/2007 | Gulati | |
| 7,268,861 B2 | 9/2007 | Treado et al. | |
| 7,268,862 B2 | 9/2007 | Treado et al. | |
| 7,277,178 B2 | 10/2007 | Shpantzer | |
| 7,295,308 B1 | 11/2007 | Samuels | |
| RE39,977 E | 1/2008 | Treado et al. | |
| 7,317,516 B2 | 1/2008 | Treado et al. | |
| 7,322,267 B1 | 1/2008 | Munson | |
| 7,362,489 B2 | 4/2008 | Wang | |
| 7,362,839 B2 | 4/2008 | Goth | |
| 7,409,299 B2 | 8/2008 | Schweitzer et al. | |
| 7,417,727 B2 | 8/2008 | Polonskiy | |
| 7,417,796 B2 | 8/2008 | Wang | |
| 7,420,664 B2 | 9/2008 | Treado | |
| 7,420,675 B2 | 9/2008 | Giakos | |
| 7,436,500 B2 | 10/2008 | Treado et al. | |
| 7,479,966 B2 | 1/2009 | Maier et al. | |
| 7,502,118 B2 | 3/2009 | Shpantzer | |
| 7,502,188 B2 | 3/2009 | Inomata | |
| 7,511,624 B2 | 3/2009 | Shaw | |
| 7,525,102 B1 | 4/2009 | Henshaw | |
| 7,551,715 B2 | 6/2009 | Rothschild | |
| 7,676,062 B2 | 3/2010 | Breed | |
| 7,679,740 B2 | 3/2010 | Neiss et al. | |
| 7,692,775 B2 | 4/2010 | Treado | |
| 7,692,776 B2 | 4/2010 | Treado | |
| 7,705,981 B2 | 4/2010 | Maier et al. | |
| 8,269,174 B2 | 9/2012 | Gardner | |
| 2001/0052979 A1 | 12/2001 | Treado | |
| 2003/0085348 A1 | 5/2003 | Megerle | |
| 2003/0123056 A1 | 7/2003 | Barnes | |
| 2004/0051867 A1 | 3/2004 | Brestel et al. | |
| 2004/0208350 A1 | 10/2004 | Rea | |
| 2005/0053270 A1 | 3/2005 | Kasai | |
| 2005/0105099 A1 | 5/2005 | Shpantzer | |
| 2005/0137806 A1 | 6/2005 | Kutsyy et al. | |
| 2005/0264813 A1 | 12/2005 | Giakos | |
| 2006/0050278 A1 * | 3/2006 | Treado et al. | 356/417 |
| 2006/0054780 A1 * | 3/2006 | Garrood et al. | 250/208.1 |
| 2006/0077255 A1 | 4/2006 | Cheng | |
| 2006/0077377 A1 | 4/2006 | Brestel et al. | |
| 2006/0100524 A1 | 5/2006 | Lucassen et al. | |
| 2006/0203238 A1 | 9/2006 | Gardner et al. | |
| 2006/0219937 A1 | 10/2006 | Henry et al. | |
| 2006/0254522 A1 | 11/2006 | Shaw | |
| 2006/0256330 A1 | 11/2006 | Leipertz | |
| 2007/0007384 A1 | 1/2007 | Sliwa | |
| 2007/0098142 A1 | 5/2007 | Rothschild | |
| 2007/0118324 A1 | 5/2007 | Gulati | |
| 2007/0125951 A1 | 6/2007 | Snider | |
| 2007/0127030 A1 | 6/2007 | Shpnatzer | |
| 2007/0139772 A1 | 6/2007 | Wang | |
| 2007/0153268 A1 | 7/2007 | Panza | |
| 2007/0166045 A1 | 7/2007 | Wang | |
| 2007/0192035 A1 | 8/2007 | Schweitzer et al. | |
| 2007/0268485 A1 | 11/2007 | Polonskiy | |
| 2007/0282506 A1 | 12/2007 | Breed | |
| 2008/0036593 A1 | 2/2008 | Rose-Pehrsson | |
| 2008/0051957 A1 | 2/2008 | Breed | |
| 2008/0062353 A1 | 3/2008 | Wang | |
| 2008/0084553 A1 | 4/2008 | Neiss et al. | |
| 2008/0129581 A1 | 6/2008 | Douglass | |
| 2008/0144885 A1 | 6/2008 | Zucherman | |
| 2008/0165344 A1 | 7/2008 | Treado et al. | |
| 2008/0191137 A1 | 8/2008 | Poteet | |
| 2008/0192246 A1 | 8/2008 | Neiss et al. | |
| 2008/0198365 A1 | 8/2008 | Treado | |
| 2008/0204757 A1 | 8/2008 | Manning | |
| 2008/0258071 A1 | 10/2008 | Arnold | |
| 2008/0268548 A1 | 10/2008 | Zuckerman | |
| 2008/0295783 A1 | 12/2008 | Furton | |
| 2008/0300826 A1 | 12/2008 | Schweitzer et al. | |
| 2009/0012723 A1 | 1/2009 | Treado et al. | |
| 2009/0021730 A1 | 1/2009 | Maier et al. | |
| 2009/0043514 A1 | 2/2009 | Schweitzer et al. | |
| 2009/0046393 A1 | 2/2009 | Davey | |
| 2009/0066947 A1 | 3/2009 | Bangalore et al. | |
| 2009/0095885 A1 | 4/2009 | Hager | |
| 2009/0101843 A1 | 4/2009 | Henshaw | |
| 2009/0128802 A1 | 5/2009 | Treado et al. | |
| 2009/0236528 A1 | 9/2009 | Shpantzer | |
| 2009/0252650 A1 | 10/2009 | Lakshmanan | |
| 2009/0257555 A1 | 10/2009 | Chalmers | |
| 2010/0051809 A1 | 3/2010 | Onat et al. | |
| 2010/0322471 A1 | 12/2010 | Treado | |
| 2011/0102565 A1 | 5/2011 | Wang | |
| 2012/0120393 A1 * | 5/2012 | Treado et al. | 356/301 |
| 2012/0140981 A1 * | 6/2012 | Berkman et al. | 382/103 |

FOREIGN PATENT DOCUMENTS

| | | |
|---|---|---|
| WO | PCT/IB2006/052448 | 1/2007 |
| WO | PCT/US2005/036593 | 1/2007 |
| WO | PCT/US2006/027172 | 3/2007 |
| WO | PCT/US2006/060158 | 3/2007 |
| WO | PCT/US2005/033740 | 4/2007 |
| WO | PCT/US2006/012300 | 4/2007 |
| WO | PCT/US2006/060683 | 5/2007 |
| WO | PCT/US2005/044648 | 7/2007 |
| WO | PCT/US2007/016040 | 7/2007 |
| WO | PCT/US06/022647 | 11/2007 |
| WO | PCT/US2006/039271 | 11/2007 |
| WO | PCT/US2007/015132 | 3/2008 |
| WO | PCT/US2007/018347 | 4/2008 |
| WO | PCT/US2007/081551 | 4/2008 |

OTHER PUBLICATIONS

Sharma, S.K. et al., Combined Remote LIBS and Raman Spectroscopy of Minerals Using a Single Laser Source, Lunar Planet Sci. XXXVIII, 2007.

Clegg, S.M. et al., LIBS-Raman Spectroscopy of Minerals Using Remote Surface Modification Techniques, Mar. 2006, Lunar Planet Sci. XXXVII.

(56) References Cited

OTHER PUBLICATIONS

Thompson, J. et al., Combined Remote LIBS and Raman Spectroscopy Measurements, Lunar Planet Sci, XXXVI, 2005.
Weins, R.C., Development of a Prototype Laser-Induced Breakdown Spectroscopy (LIBS) Instrument and Stand-off Raman Capabilities as Part of the Mars Instrument Development Program, Lunar Planet Sci., XXXI.
Poster-Session: Mars Polar Science, Astrobiology, Future Missions/Instruments and Other Mars Science, Jul. 2007, Secenth International Conference on Mars, Session 11.
Marquardt, Brian J. et al., Novel Probe for Laser-induced Breakdown Spectroscopy and Raman Measurements Using an Imaging Optical Fiber (Jun. 1998) vol. 52, No. 9.
Extended European Search Report, PCT/US2006/0022647, mailed on Aug. 10, 2010.
Nelson et al., "Single-Shot Mulitwavelength Imaging of Laser Plums," Applied Spectroscopy, vol. 52, No. 2, 1998.
John Watkinson, "The Engineer's Guide to Motion Compensation," Snell & Wilcox, 1994.available at: http.//www.snellwilcox.com/community/knowledge_center/engineering_guides?emotion.pdf>.
Office Action, U.S. Appl. No. 11/632,471, Feb. 17, 2008.
Office Action, U.S. Appl. No. 11/632,471, Apr. 3, 2009.
Office Action, U.S. Appl. No. 11/632,471, Apr. 16, 2008.
Office Action, U.S. Appl. No. 11/645,132, Apr. 1, 2009.

* cited by examiner

CONDOR-ST

CONDOR-ST (Gen3 Breadboard)

CONDOR-ST (Gen2)

Integrated CONDOR-ST (Gen2 & Gen3)

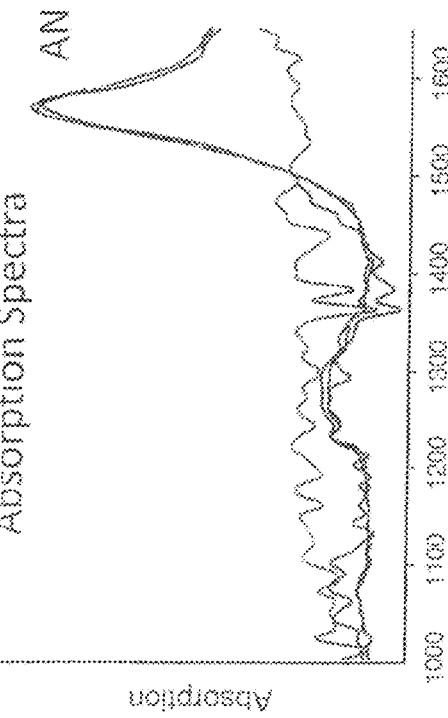
Figure 5B
Absorption Spectra
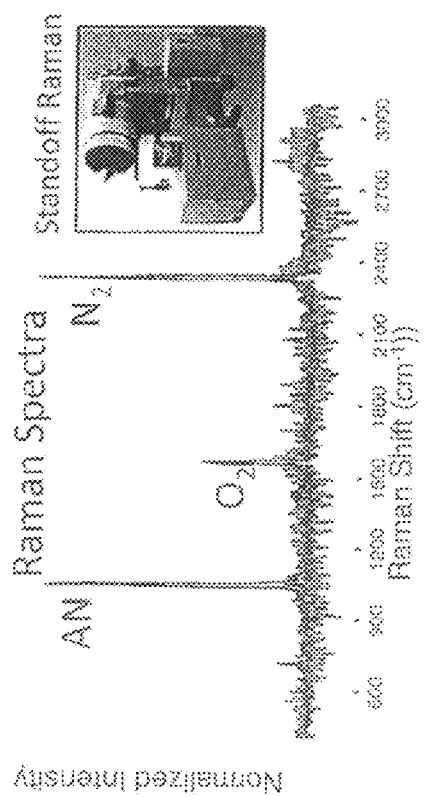
Figure 5E
Raman Spectra
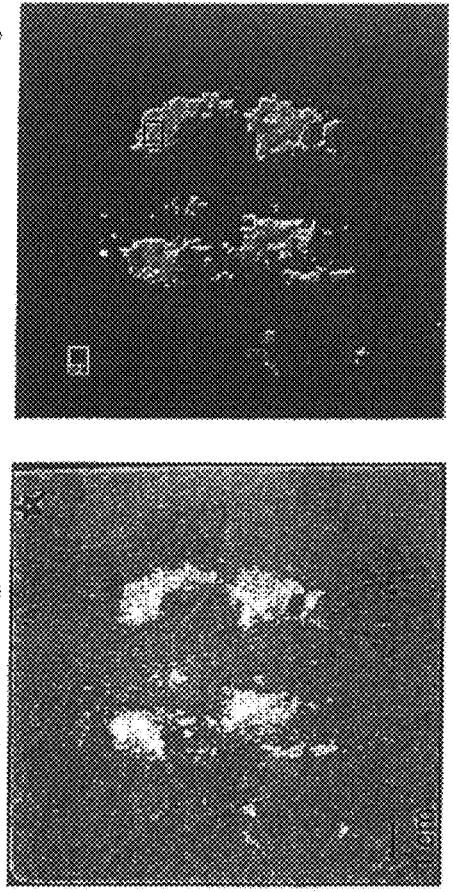
Figure 5B
1570nm NIR Chemical Image
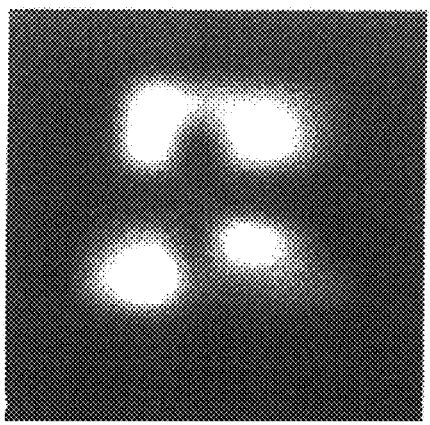
Figure 5D
Bicubic Expansion
Figure 5A
Optical Image
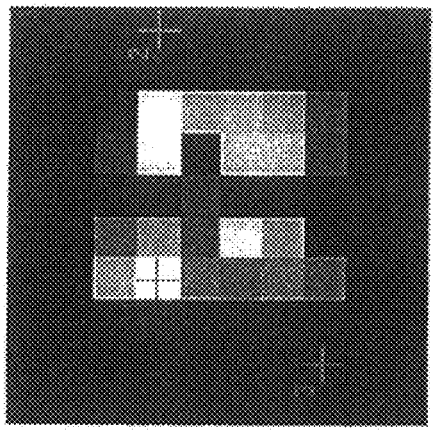
Figure 5C
1046 cm⁻¹ Raman Image

CONDOR-ST Sensitivity Enhancement
*Gen2 vs Gen3 50m AN Fingerprints on Slate Surface*

Figure 6A Digital Photograph
Figure 6B Gen3 NIR Image
Figure 6C Gen2 NIR Image
Figure 6D Absorption Spectra

- Condor-ST (G2) boresighted at 70m
- Condor-ST (G2) at 60m range to Target 112
- Condor-ST (G2) DE detection at stand off range to Target 117 of 210m Disturbed earth at a 200m standoff range On the Move detection simulated by panning of PTU across road.

Identification of camouflage EFP, Disturbed Earth and Command Wire

SYSTEM AND METHODS FOR EXPLOSIVES DETECTION USING SWIR

RELATED APPLICATIONS

This Application is a continuation-in-part of pending U.S. patent application Ser. No. 12/754,229, filed on Apr. 5, 2010, entitled "Chemical Imaging Explosives (CHIMED) Optical Sensor using SWIR." This Application also claims priority to the following U.S. Provisional Patent Application No. 61/335,785, filed on Jan. 12, 2010, entitled "System and Method for SWIR HSI for Daytime and Nighttime Operations," No. 61/278,393, filed on Oct. 6, 2009, entitled "Use of Magnification to Increase SWIR HSI Detection Sensitivity," No. 61/301,814, filed on Feb. 5, 2010, entitled "System and Method for Detecting Hazardous Agents Including Explosives," No. 61/305,667, filed on Feb. 18, 2010, entitled "System and Method for Detecting Explosives on Shoes and Clothing," No. 61/403,141, filed on Sep. 10, 2010, entitled "Systems and Methods for Improving Imaging Technology", No. 61/324,963, filed on Apr. 16, 2010, "Short-Wavelength Infrared (SWIR) Multi-Conjugate Liquid Crystal Tunable Filter." These patent and patent applications are hereby incorporated by reference in their entireties.

This invention was made with government support under Contract Number W911NF-09-C-0078 awarded by US Army RDECOM. The government has certain rights in the invention

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NW), short-wave infrared (SWIR), mid infrared (MIR) wavelengths and to some overlapping ranges. These correspond to wavelengths of about 180-380 nm (UV), 380-700 nm (VIS), 700-2500 nm (NW), 900-1700 nm (SWIR), and 2500-25000 nm (MIR).

There currently exists a need for accurate detection of explosives and explosive residues. In particular, there exists a need for accurate and reliable detection of explosives and explosive residues in standoff and on-the-move (OTM) configurations. There exists a need for a compact multispectral sensor that is capable of both daytime and covert, eye-safe nighttime operations.

SUMMARY OF THE INVENTION

The present disclosure relates to systems and methods for explosive detection using spectroscopic methods, including imaging. More specifically, the present disclosure provides for systems and methods for explosive detection using short wave infrared (SWIR) hyperspectral imaging. The present disclosure provides for systems and methods that may operate using both passive and active illumination modalities. Therefore, the systems and methods disclosed herein hold potential or daytime and nighttime configurations.

The present disclosure provides for a system and method for the standoff detection of explosives using infrared, including SWIR, spectroscopic methods. In one embodiment, the invention described herein enables the passive, standoff detection of IED components while On-the-Move ("OTM"). Active illumination can also be used. The system and method can be used to detect Improvised Explosive Devices ("IEDs") and emplacements (such as DE and aged concrete), command wires, EFP camouflage, and explosive residue, among other materials. The system and method described herein hold potential for enabling the automated/aided anomaly detection OTM during day and/or night conditions aboard ground vehicles. The embodiments also hold potential for the operators to assess a route and detonate threats.

Explosive detection and identification may be accomplished by spectrally filtering SWIR light reflected by the target area in the 900 to 1700 nm wavelength region. Most materials of interest show molecular absorption in this region. In one embodiment, the sun or a broadband IR lamp may be used as the light source in a reflected light configuration. Data may be captured by rapid tuning of the MCF to a spectral band of interest followed by capturing an image of the scene with the InGaAs FPA. These images can be rapidly processed to create chemical images in real-time. This may result in images where the observed contrast is due to the presence or absence of a particular chemical or explosive material or device. The same system may, in another embodiment, be used to detect disturbed earth associated with an emplacement based on scattering property differences associated with disturbed and undisturbed earth in the SWIR spectral region.

BRIEF DESCRIPTION OF THE DRAWINGS

The Accompanying drawings, which are included to provide further understanding of the disclosure and are incorporated in and constitute a part of this specification, illustrate embodiments of the disclosure and together with the description, serve to explain the principles of the disclosure. The patent or application file contains at least one drawing executed in color. Copies of this patent or patent application publication with color drawing(s) will be provided by the Office upon request and payment of the necessary fee.

In the drawings:

FIG. 5 is illustrative of the sensitivity capabilities of the system and method of the present disclosure.

DETAILED DESCRIPTION

Reference will now be made in detail to the preferred embodiments of the present disclosure, examples of which are illustrated in the accompanying drawings. Wherever possible, the same reference numbers will be used throughout the drawings to refer to the same or like parts.

Figure 1:
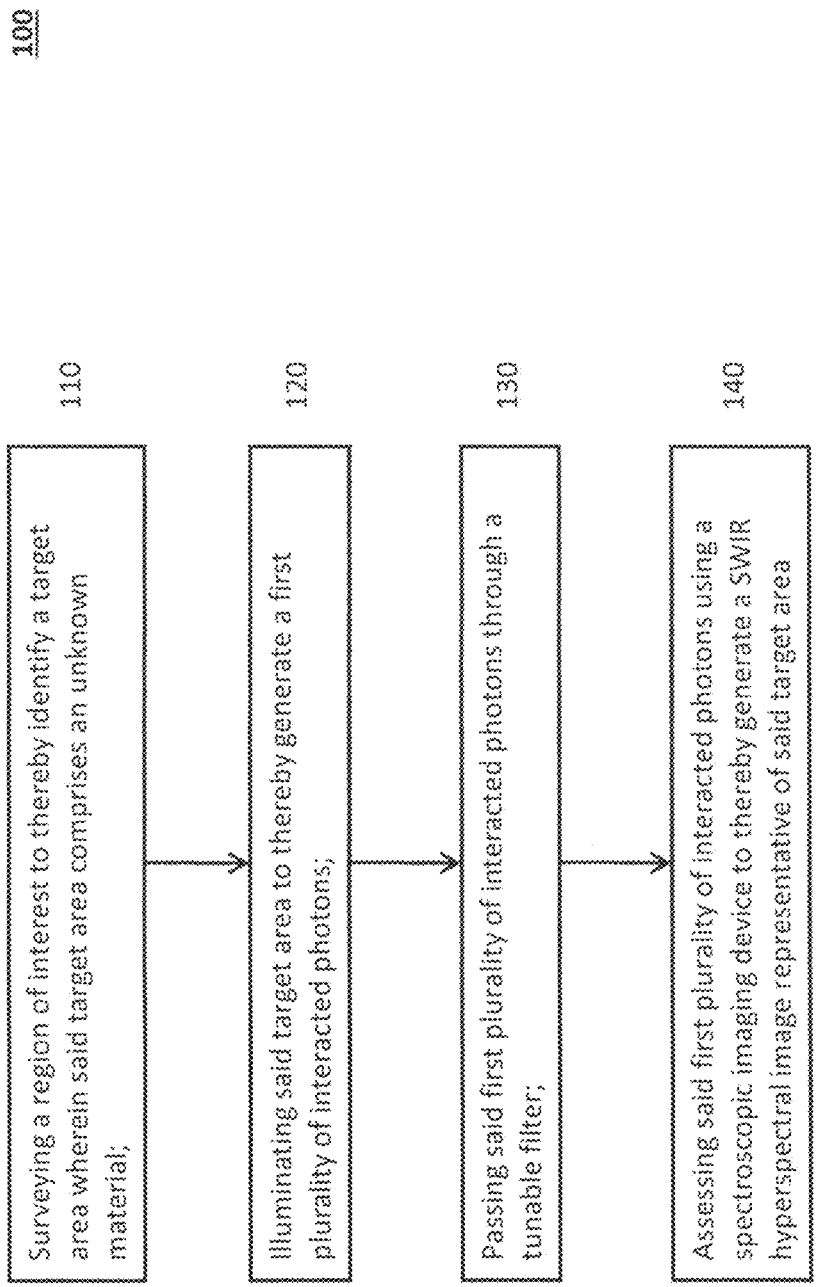
FIG. 1 is illustrative of a method of the present disclosure.

FIG. 1 is representative of a method of the present disclosure. The method 100 may comprise surveying a region of interest to thereby identify a target area wherein said target area comprises an unknown material in step 110. In step 120 the target area is illuminated to thereby generate a first plurality of interacted photons. In one embodiment, the first plurality of interacted photons may comprise photons selected from the group consisting of: photons reflected by a target area, photons absorbed by a target area, photons scattered by a target area, photons emitted by a target area, and combinations thereof. In step 130 the first plurality of interacted photons are passed through a tunable filter. The first plurality of interacted photons are assessed using a spectroscopic imaging device to thereby generate a SWIR hyperspectral image representative of the target area in step 140.

In one embodiment, the method may further comprise analyzing said SWIR hyperspectral image to thereby detect and/or identify said unknown material. In one embodiment this unknown material may comprise an explosive selected from the group consisting of: nitrocellulose, Ammonium nitrate ("AN"), nitroglycerin, 1,3,5-trinitroperhydro-1,3,5-triazine ("RDX"), 1,3,5,7-tetranitroperhydro-2,3,5,7-tetrazocine ("HMX") and 1,3,-Dinitrato-2,2-bis(nitratomethyl) propane ("PETN").

In one embodiment, analyzing a SWIR hyperspectral image may comprise comparing at least one of a SWIR hyperspectral image and/or one or more SWIR spectra associated with said SWIR hyperspectral image with a reference data base wherein the reference data base comprises at least one reference SWIR data base associated with a known material. The reference data base may also comprise at least one reference visible data set associated with a known material. This reference data base may be consulted during surveying of a region of interest. In one embodiment, this comparing may be accomplished using one or more chemometric techniques. This chemometric technique may be selected from the group consisting of: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion, and combinations thereof.

In one embodiment, the method may further comprise obtaining at least one of a MWIR hyperspectral image, a LWIR hyperspectral image, and combinations thereof. In another embodiment, the method may further comprise applying a fusion algorithm to at least two of: a visible image, a SWIR hyperspectral image, a MWIR hyperspectral image, a LWIR hyperspectral image, and combinations thereof.

In one embodiment, the region of interest may be surveyed using a visible imaging device. In one embodiment, this visible image device may output a dynamic image of a region of interest. This dynamic image may be output in real time. In one embodiment the visible imaging device may comprise a video capture device. In another embodiment, the visible imaging device may comprise a RGB camera.

In another embodiment, the region of interest may be surveyed using a SWIR spectroscopic imaging device. In such an embodiment, SWIR hyperspectral imaging may be used to both survey a region of interest to locate a target area and also to interrogate the target area to detect and/or identify an unknown material.

One or more target areas present in a region of interest may be located by analyzing a visible image output by a visible imaging device. In one embodiment, the target area may be located based on morphological features. These features may include but are not limited to: size of the target area, shape of the target area, and color of the target area, and combinations thereof.

In one embodiment, the SWIR hyperspectral image may comprise a digital image and a spatially resolved SWIR spectra for each pixel in said image. In one embodiment, the SWIR hyperspectral image may comprise a dynamic chemical image.

In one embodiment illumination of at least one of a region of interest and a target area is achieved using an illumination source selected from the group consisting of: a laser illumination source, a broadband light source, and a laser light source, and combinations thereof.

In one embodiment, telescope optics may be configured for at least one of: locating and focusing on a target area and/or collecting said first plurality of interacted photons. In one embodiment, a telescope optics may be implemented to enable magnification and thereby SWIR hyperspectral imaging sensitivity.

In one embodiment, the tunable filter may be selected from the group consisting of: a SWIR multi-conjugate liquid crystal tunable filter, a SWIR liquid crystal tunable filter, a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter, and combinations thereof.

In one embodiment, the system and method utilize ChemImage Multi-Conjugate Filter ("MCF") technology available from ChemImage Corporation, Pittsburgh, Pa. A multi-conjugate filter, a type of liquid crystal tunable filter (LCTF), consists of a series of stages composed of polarizers, retarders and liquid crystals. The multi-conjugate filter is capable of providing diffraction limited spatial resolution, and a spectral resolution consistent with a single stage dispersive monochromator. A multi-conjugate filter may be computer controlled with no moving parts. It may be tuned to any wavelength in the given filter range. This results in an essentially infinite number of spectral bands available. Compared to earlier generation LCTFs, a multi-conjugate filter provides high optical throughput, superior out-of-band rejection and faster tuning speeds. While images associated with spectral bands of interest must be collected individually, material-specific chemical images revealing target detections may be acquired, processed and displayed in numerous times each second. Combining MCF technology with software targeting algorithms is central to the performance and ability of OTM SWIR HSI detection.

This technology is more fully described in U.S. Pat. No. 7,362,489, entitled "Multi-Conjugate Liquid Crystal Tunable Filter" and U.S. Pat. No. 6,992,809, also entitled "Multi-Conjugate Liquid Crystal Tunable Filter." Both of these patents are hereby incorporated by reference in their entireties.

The systems and methods of the present disclosure may incorporate or comprise CONDOR-ST technology available from ChemImage Corporation, Pittsburgh, Pa.

Figure 2:
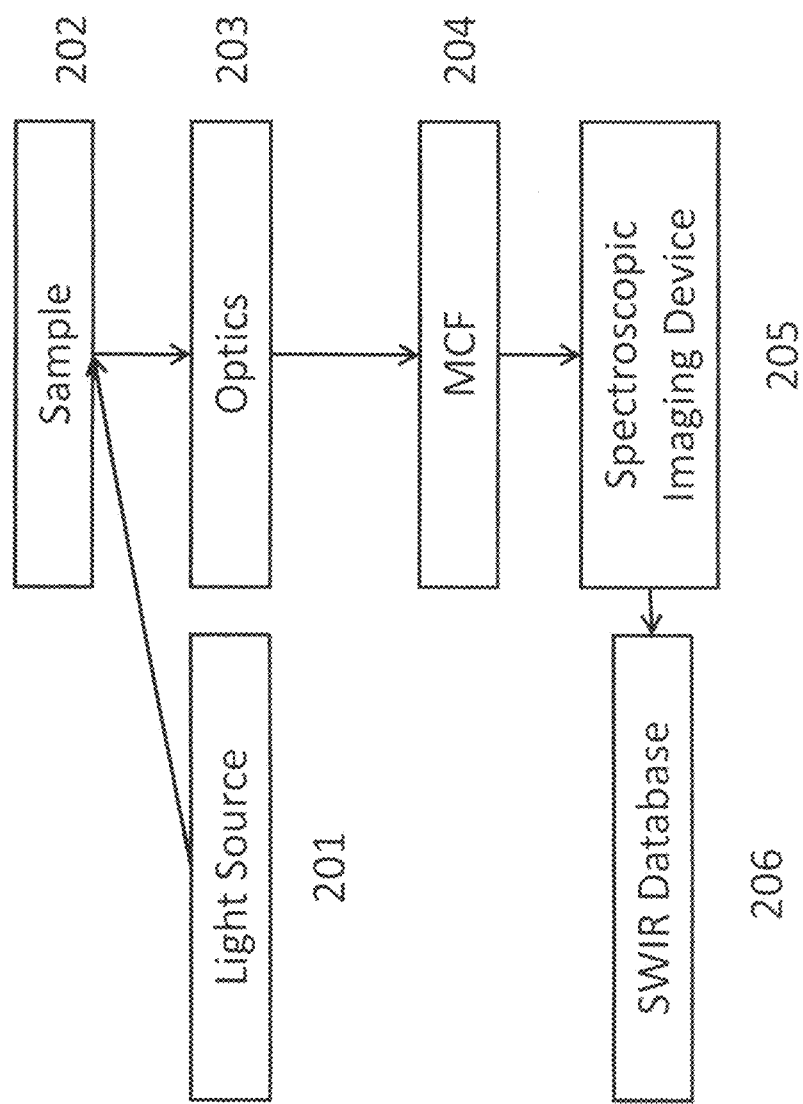
FIG. 2 is a schematic representation of a system of the present disclosure.

The present disclosure also provides for a system for detecting and/or identifying explosive materials. FIG. 2 is a schematic representation of a system of the present disclosure. The system 200 may comprise an illumination light source 201 configured to illuminate a unknown sample 202 to thereby generate a plurality of interacted photons. In one embodiment, the illumination light source 201 may be selected from the group consisting of: a laser illumination source, a broadband light source, an ambient light source, and combinations thereof. In one embodiment, the system 200 may be configured for passive illumination, active illumination, and combinations thereof.

These interacted photons may be collected by one or more optics 203 and passed through a tunable filer. The tunable filter in FIG. 2 is illustrated as a multi-conjugate liquid crystal tunable filter 204.

As discussed above, the multi-conjugate liquid crystal tunable filter may be used to filter light to the detector and is capable of tuning to an infinite number of spectral bands, therefore, for nighttime operation using active broadband IR illumination, decreasing spectral resolution may not be necessary. Nighttime operation of the system may cover the same spectral range and is capable of the same number of spectral bands as daytime operation. Transition from daytime to nighttime operations should be as simple as switching on a lamp.

For daytime operation, one embodiment provides for the use of the sun as an illumination source for the scene being interrogated. In one embodiment, the system comprises an active illumination subsystem to allow for nighttime operations. A set of tungsten white light illumination sources may be used in one embodiment to allow for nighttime detection. Tungsten white light alone is eye safe but is not invisible to visible sensors. By coupling the tungsten white light sources with IR long pass filters all visible light will be blocked and only IR light will illuminate the scene. SNR modeling efforts will assist in determining the type, power and number of tungsten lamps and filter combinations required to achieve the standoff distance requirement. In one embodiment, four (4) spotlights with 5900 lumens each, with 6° angular divergence would produce an average intensity of ~1100 and ~5 m illumination diameter at 50 m standoff. Additional lighting may be used to carry out measurements at standoff distances of 200-1000 m.

However, the present disclosure contemplates that other tunable filters known in the art may be used in other embodiments. The tunable filter 204 sequentially filters the plurality of interacted photons into a plurality of wavelength bands. The plurality of interacted photons are detected using a spectroscopic imaging device 205. The spectroscopic imaging device may be configured to generate a SWIR hyperspectral image representative of the unknown sample interrogated. In another embodiment, the spectroscopic imaging device may be configured so as to generate at least one of: a plurality of spatially resolved SWIR images, a plurality of spatially resolved SWIR spectra, a SWIR chemical image, and combinations thereof.

The system 200 may further comprise a reference data base comprising at least one SWIR reference data set. This is illustrated in FIG. 2 as a SWIR database 206.

Figure 3:
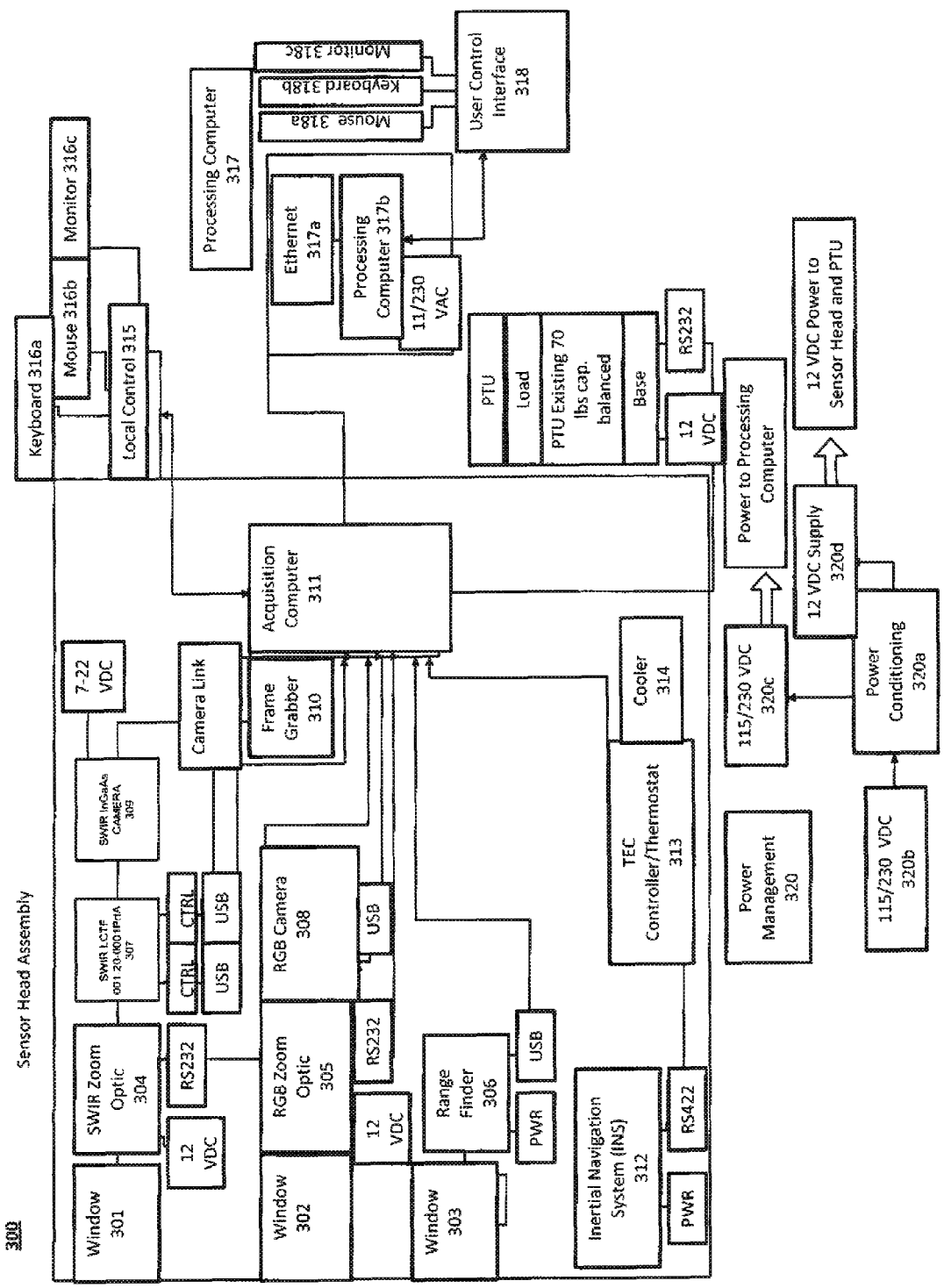
FIG. 3 is a schematic representation of a system of the present disclosure.

FIG. 3 is a more detailed schematic of a system of the present disclosure. The system 300 may comprise one or more windows 301, 302, and 303, which may also be referred to as collection lenses, or lenses, herein. The system may comprise a one or more zoom optics. In one embodiment, a SWIR zoom optic 304 may be operatively coupled to a tunable filter. In FIG. 3, the tunable filter is illustrated as a SWIR liquid crystal tunable filter 307. In another embodiment, the filter may comprise a SWIR multi-conjugate liquid crystal tunable filter. The SWIR liquid crystal tunable filter may 307 may be configured to effectively separate a plurality of interacted photons into a plurality of predetermined wavelength bands. The plurality of interacted photons may be detected by a SWIR detector, illustrated in FIG. 309 as a SWIR InGaAs Camera. However, other embodiments may comprise other detectors known in the art including but not limited to a CCD and a ICCD. In one embodiment is SWIR camera 309 may be operatively coupled to a frame grabber 310.

The system 300 may further comprise a visible zoom optic, illustrated in FIG. 3 as a RGB zoom optic 305. This RGB zoom optic 305 may be operatively coupled to visible detector. The visible detector in FIG. 3 is illustrated as an RGB camera 308. However, this visible detector may also comprise a video capture device.

The system 300 may further comprise a range finder 306. In one embodiment, at least one of a frame grabber 310, a RGB camera 308, a range finder 306, and an inertial navigation system 312 may be operatively coupled to an acquisition computer 311. This acquisition computer 312 may further, in one embodiment, be coupled to at least one of: a local computer 315, a processing computer 317, and a PTU 319. In one embodiment, a local computer 315 may comprise at least one of: a keyboard 316a, a mouse 316b, and a monitor 316c. In one embodiment, a processing computer 317 may comprise at least one of: a Ethernet configuration 317a, and a second processing computer 317b. The processing computer 317 may be operatively coupled to a user control interface system 318. The user control interface system 318 may comprise at least one of: a mouse 318a, keyboard 318b, and monitor 318c. The system may further comprise a power management system 320 may be operatively coupled to the system 300.

In one embodiment, the system of the present disclosure may incorporate a high pixel resolution, high frame rate color video camera system to assist in locating targets of interest. The SWIR HSI portion of the system may consist of an InGaAs focal plane camera coupled to a wavelength-agile Multi-Conjugate Filter (MCF) in combination with a zoom optic capable of viewing a large area, or imaging a localized area at high magnification. In one embodiment of operation, an area would first be screened using the wide field setting on the zoom lens. Once the area is screened and potential targets are identified, confirmation of the area may be accomplished as necessary by using the narrow field setting on the zoom lens.

In one embodiment, at least one illumination source will incorporate IR long pass filters to eliminate any visible light emitted from the source(s) and allow for only IR light to illuminate the scene. The IR light is eye safe and invisible to visible sensors.

Figure 4B:
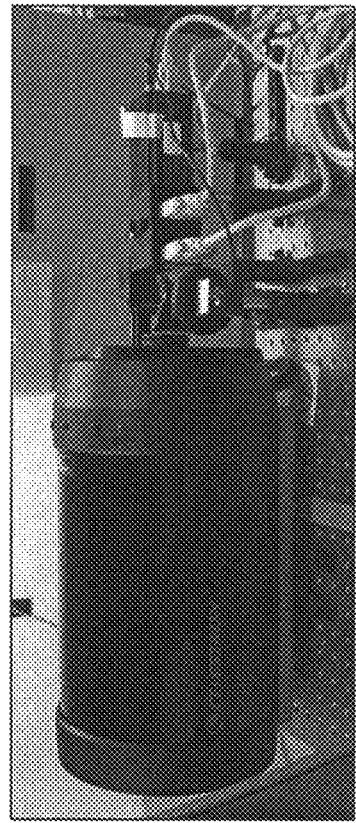
FIG. 4 is illustrative of exemplary packaging options of the systems of the present discourse.
Figure 4A:
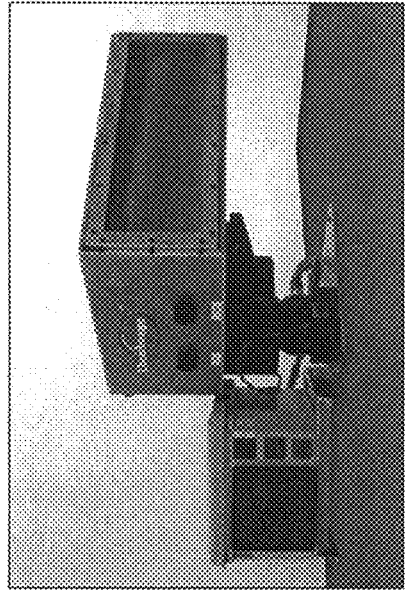
Figure 4C:
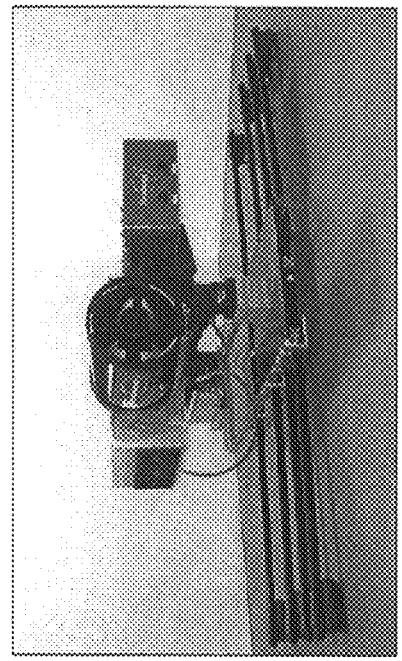
Figure 6E:
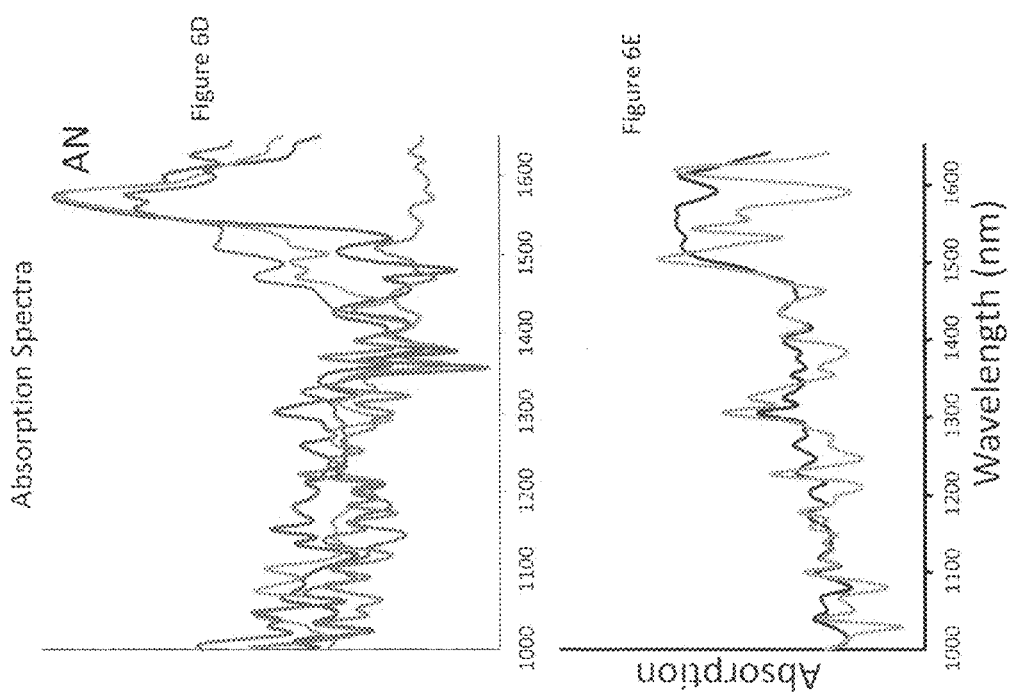
FIG. 6 is illustrative of the sensitivity capabilities of the system and method of the present disclosure.
Figure 6E:
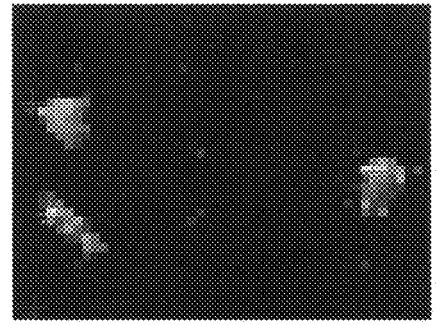
Figure 6E:
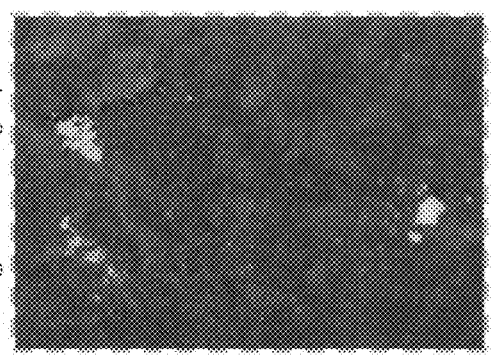

FIGS. 4A-4C are illustrative of exemplary embodiments of packaging of the systems of the present disclosure. In one embodiment, a 20× magnification increase is used to increase SWIR HSI detection sensitivity. In one example, the feasibility of increasing CONDOR-ST sensitivity by integration of an 8" diameter telescope (Gen 3 breadboard) was demonstrated. Ammonium nitrate (AN) fingerprints were prepared on three substrates (aluminum sheet metal, slate tile and dust/dirt covered slate tile) by fingerprint transfer of AN particles directly on the substrates. Three sensors were used to characterize the samples placed at a 50 m standoff distance—namely, the Raman standoff, CONDOR-ST (Gen 2) and CONDOR-ST (Gen3 Breadboard) sensors. Conclusions included the following: Gen 3 breadboard provides superior spatial image fidelity over Gen 2 (~1 mm/pixel compared to 20 mm/pixel), Gen 3 breadboard provides superior sensitivity over Gen 2 due in part to the improved spatial resolution, and Gen 3 breadboard field of view is narrowed to 43 cm×23 cm (at 50 m). See FIGS. 5 and 6. FIG. 5 depicts exemplary Optical Image (FIG. 5A), NIR chemical image (FIG. 5B), Raman image (FIG. 5C), and Bicubic Expansion (FIG. 5D). Absorption spectra and Raman spectra are depicted in FIGS. 5E and 5F, respectively. FIG. 6 depicts exemplary digital photographs (FIG. 6A), Gen3 NIR Image (FIG. 6B) and Gen 2 NIR image (FIG. 6C). Absorption spectra are depicted in FIGS. 6D and 6E, respectively.

Figure 7:
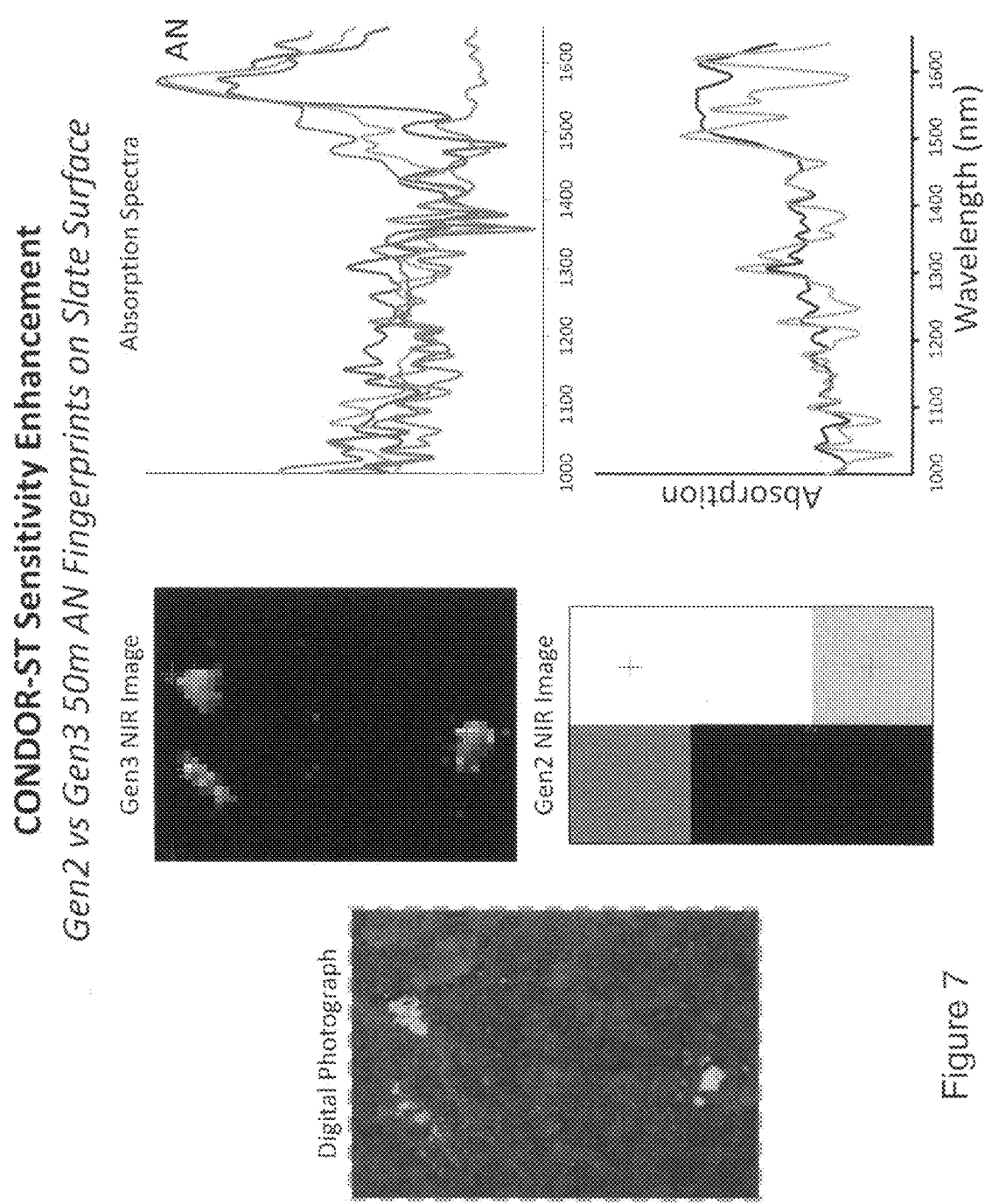
FIG. 7 is illustrative of the sensitivity capabilities of the system and method of the present disclosure.
Figure 8:
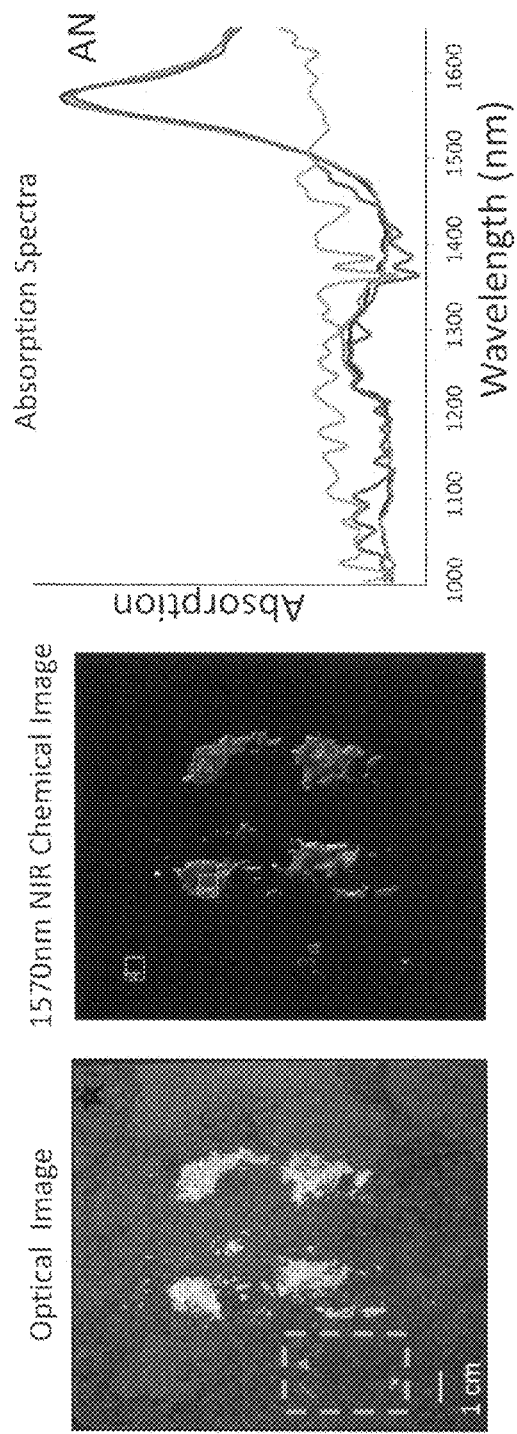
FIG. 8 is illustrative of the sensitivity capabilities of the system and method of the present disclosure.
Figure 9:
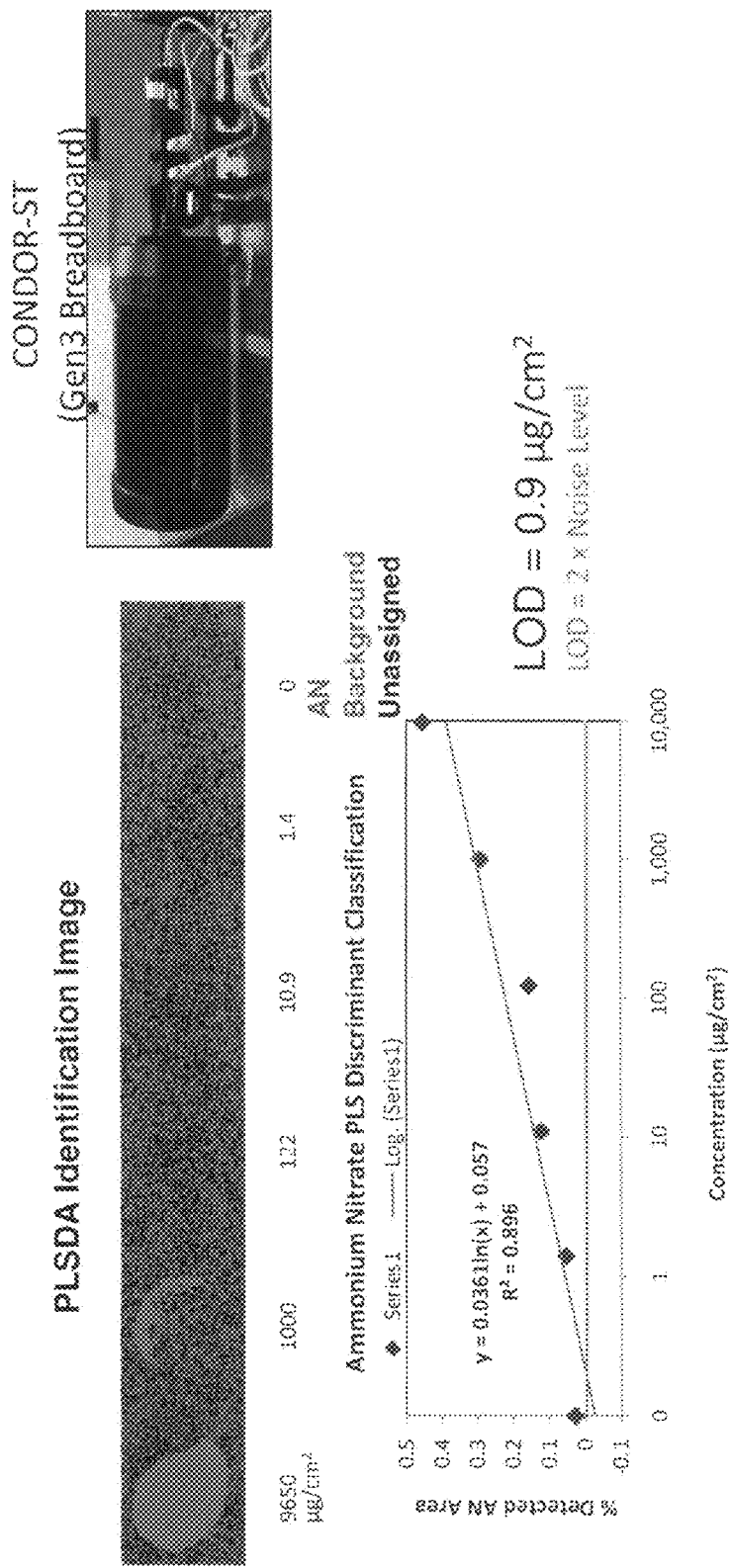
FIG. 9 is illustrative of the sensitivity capabilities of the system and method of the present disclosure.
Figure 10A:
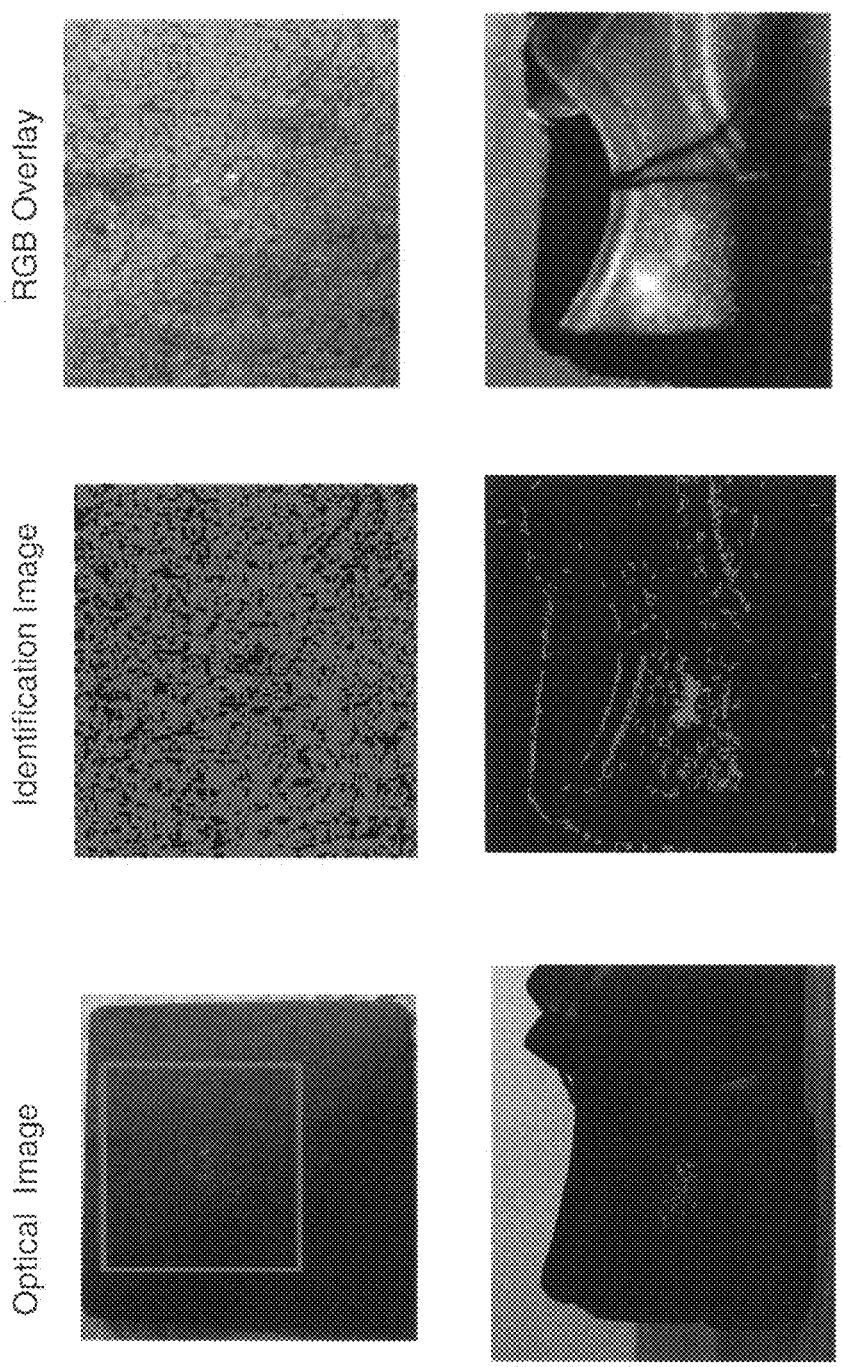
FIG. 10A is illustrative of detection of explosive residue on a shoe.
Figure 10B:
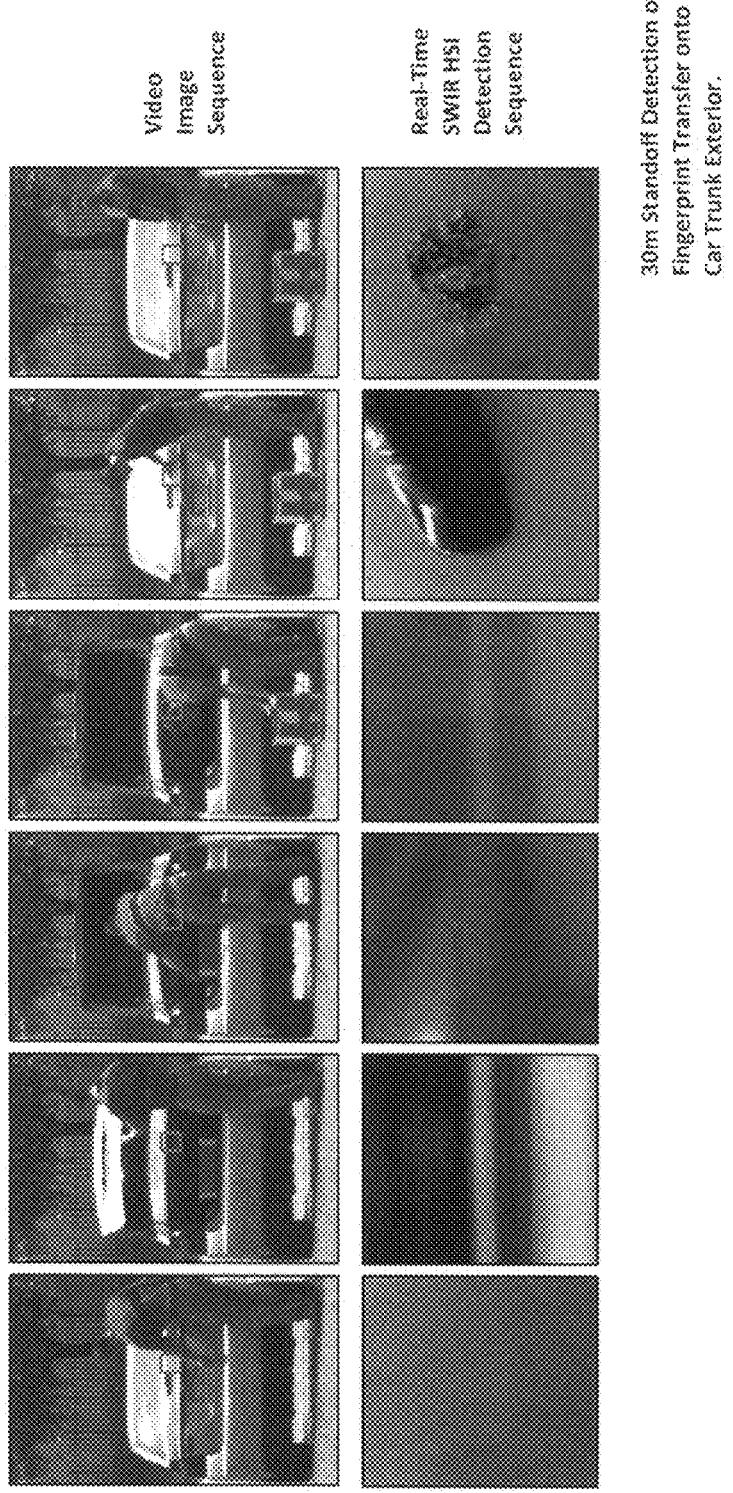
FIG. 10B is illustrative of detection of explosive residue on a car trunk surface.
Figure 11:
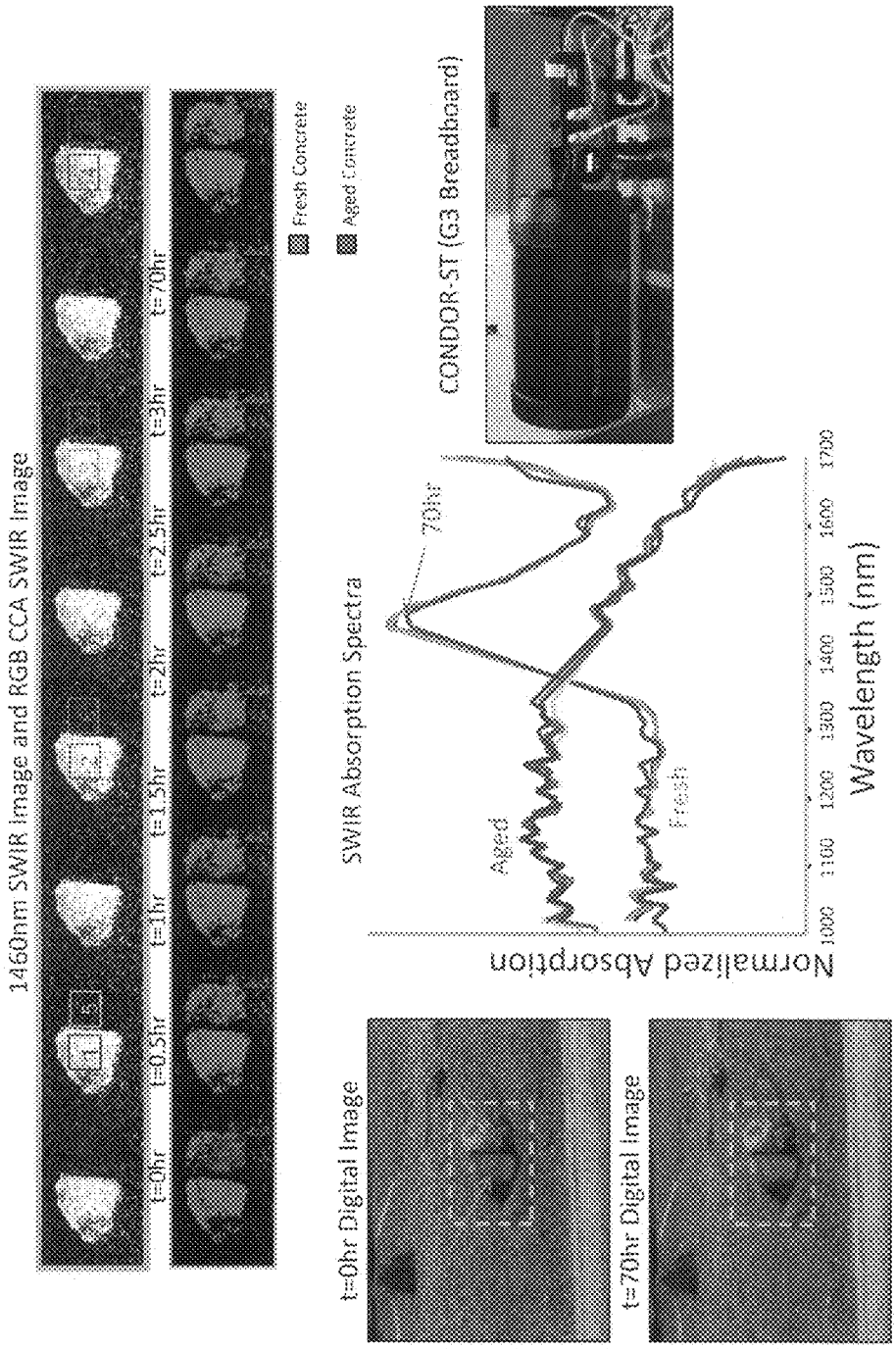
FIG. 11 is illustrative of the capability of the present disclosure to distinguish between aged and new concrete.
Figure 12:
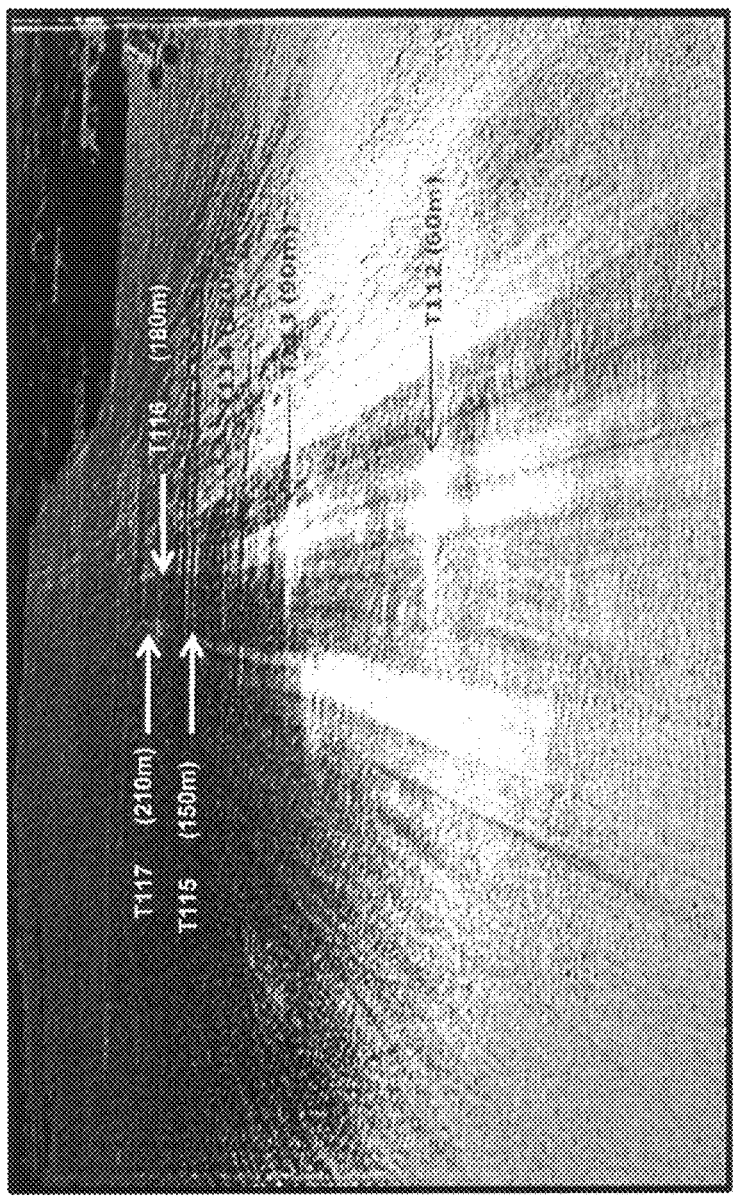
FIG. 12 is illustrative of the capability of the present disclosure to detect disturbed earth.

FIGS. 7-12 provide further support of the detection capabilities of the present disclosure. Included in these Figures is evidence of the sensitivity enhancement capabilities of the system and method of the present disclosure. FIG. 7 is illustrative of the detection of AN on fingerprints on a slate surface obtained using a Gen3 sensor at 50 m standoff distance. FIG. 8 is illustrative of a comparison between Gen2 and Gen3 sensors. The comparison is illustrative of the detection of AN on fingerprints on a slate surface at 50 m standoff distance. FIG. 9 is also illustrative of CONDOR-ST sensitivity enhancements. By increasing magnification of the image gathering optics, sensitivity of the CONDOR-ST SWIR HSI system can be increased. The sample in FIG. 9 comprises Ammonium nitrate (AN) on substrates (aluminum sheet metal, slate tile, dust/dirt covered slate tile, shoe) by fingerprint transfer. The sensor used to obtain the results was a CONDOR-ST (Gen3) sensor with a 8" diameter telescope. FIG. 10A is illustrative of the detection of AN fingerprints at 50 m standoff range on a shoe. This illustrates the potential of the CONDOR-ST SWIR HSI sensor for detection of explosive materials on a variety of materials. Such application is more fully described in U.S. patent application Ser. No. 12/754,229, filed on Apr. 5, 2010, entitled "Chemical Imaging Explosives (CHIMED) Optical Sensor using SWIR", which is hereby incorporated by reference in its entirety. FIG. 10B is illustrative of detection of AN fingerprint residue transferred by touching a car trunk surface. This data was obtained at 20 m standoff range in real-time. FIG. 11 is illustrative of the ability of the system and method of the present disclosure to detect between aged and fresh concrete. FIG. 12 is illustrative of the ability of the system and method of the present disclosure to detect disturbed earth at a 200 m standoff range.

In one embodiment, the systems and methods of the present disclosure may be configured to operate in at least one of the following configurations: proximal detection, standoff detection, stationary detection, and on-the-move detection. Standoff detection of explosives is more fully described in the following U.S. Patents and Patent Applications, which are hereby incorporated by reference in their entireties: U.S. Pat. No. 7,692,775, filed on Jun. 9, 2006, entitled "Time and Space Resolved Standoff Hyperspectral IED Explosives LIDAR Detection", Ser. No. 12/199,145, filed on Aug. 27, 2008, entitled "Time and Space Resolved Standoff Hyperspectral IED Explosives LIDAR Detection", Ser. No. 12/802,994, filed on Jun. 17, 2010, entitled "SWIR Targeted Agile Raman (STAR) System for Detection of Emplace Explosives."

Figures 13A, 13B:
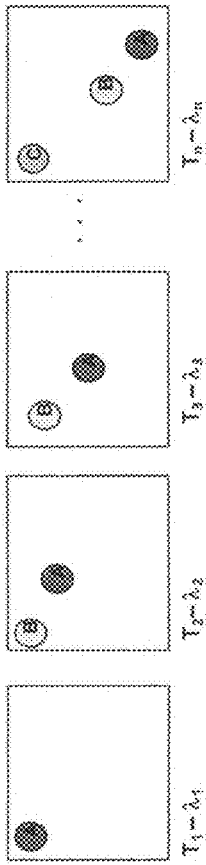
FIG. 13A is illustrative of a method of the present disclosure that may enable on-the-move detection.
FIG. 13B is illustrative of exemplary integration times of an on-the-move detection configuration of the present disclosure.
Figure 14:
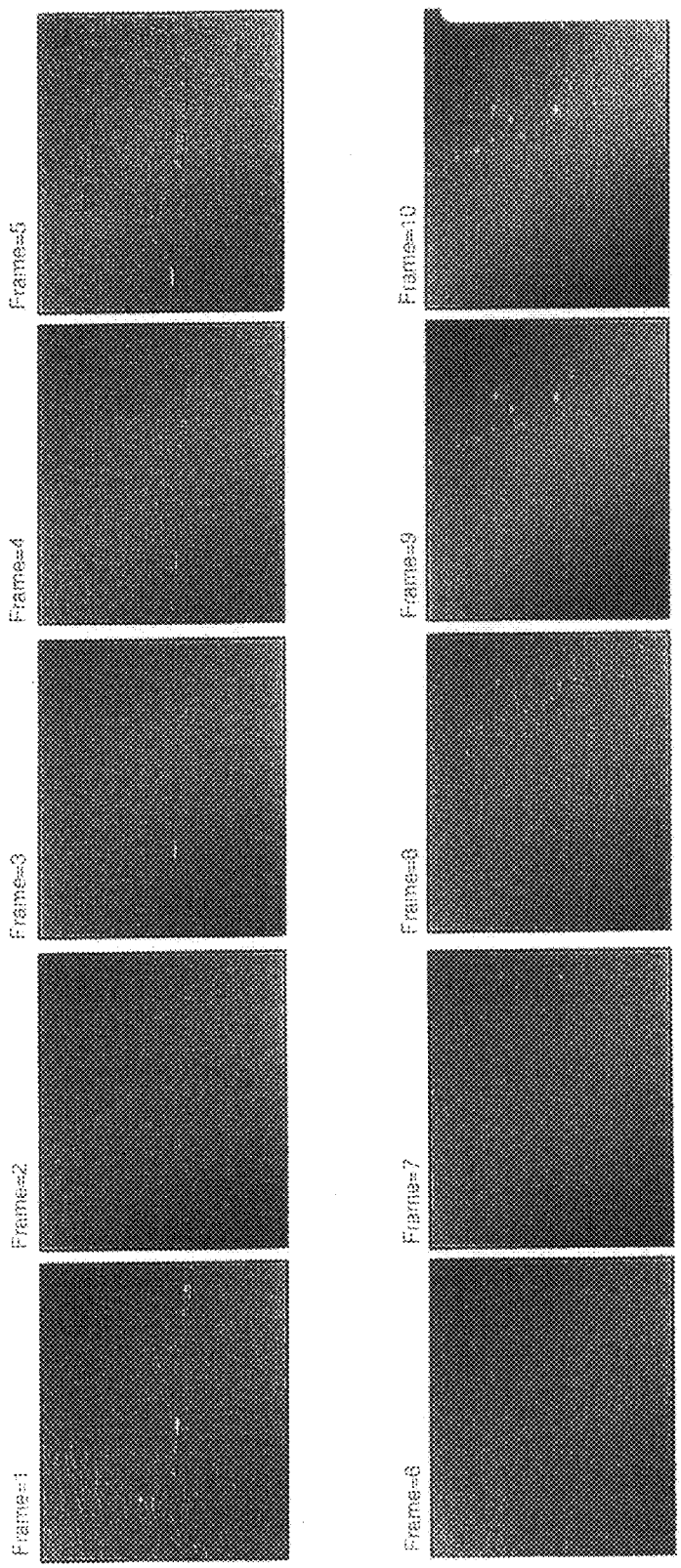
FIG. 14 is of on the move detection using a system of the present disclosure.
Figure 15:
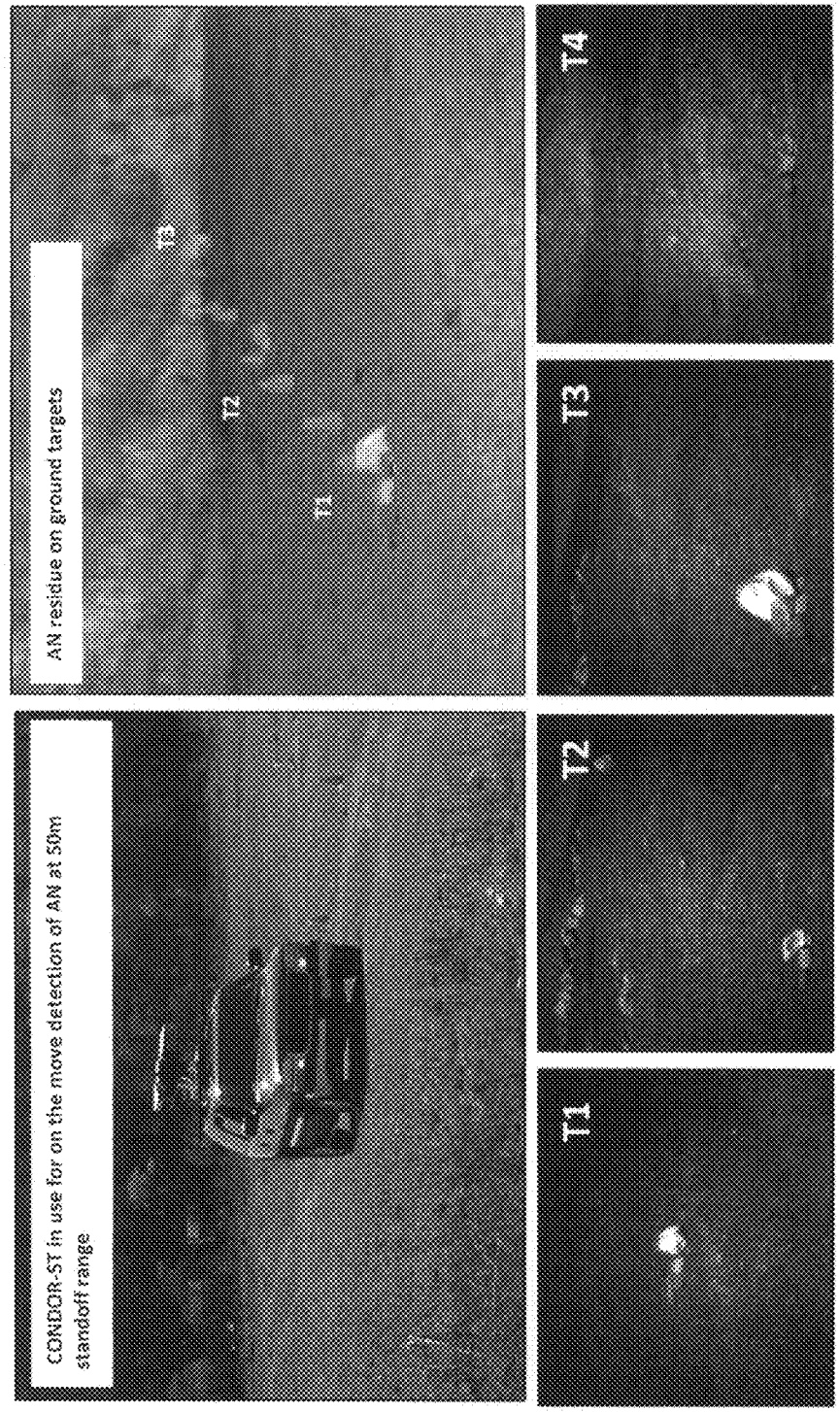
FIG. 15 is illustrative of the capability of the present disclosure to perform on-the-move detection.
Figure 16:
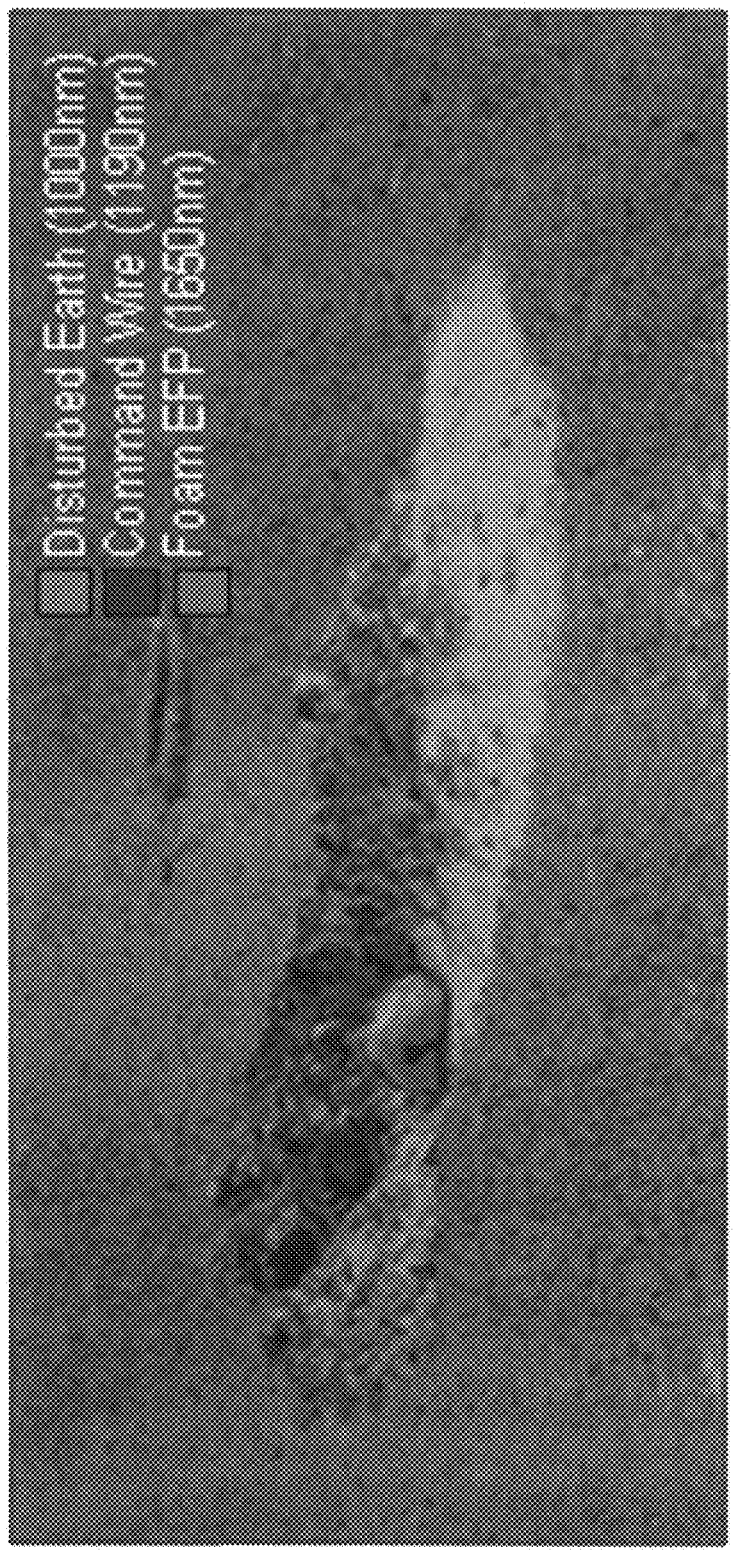
FIG. 16 is illustrative of the capability of the present disclosure to detect and distinguish between multiple materials in a scene.

In one embodiment, the system of the present disclosure may be used for stationary and On-the-Move ("OTM") explosive detection, disturbed earth detection and camouflage concealment and detection. In one embodiment, on-the-move detection may be enabled by using dynamic imaging in one or more modalities including visible and SWIR. FIGS. 13A and 13B are provided to further explain on-the-move detection according to one embodiment of the present disclosure. The present disclosure also provides for a system and method of dynamic chemical imaging in which more than one object of interest passes continuously through the FOV. Such continuous stream of objects, results in the average amount of time required to collect all frames for a given object being equivalent to the amount of time to capture one frame as the total number of frames under collection approaches infinity (frame collection rate reaches steady state). In other words, the system is continually collecting the frames of data for multiple objects simultaneously and with every new frame, the set of frames for any single object is completed. In one embodiment, the objects of interest are of a size substantially smaller than the FOV to allow more than one object to be in the FOV at any given time. Referring to FIG. 13A, on-the-move detection may be enabled by collecting each frame at a different wavelengths. One or more objects may be present in slightly translated positions in each image frame acquired. Tracking of objects across all n frames allows the spectrum to be generated for each pixel in the object. The same process may be followed for all objects in the frames. A continual stream of objects will be imaged with defined wavelengths at defined time intervals. This methodology may also utilize the benefits of signal averaging. FIG. 13B is provided to illustrate approximate integration times associated with the configuration of FIG. 13A. FIG. 14 is illustrative of on-the-move detection simulated by panning of PTU across a road. FIG. 15 is illustrative of on-the-move detection of AN residue deposited on the ground at a standoff range of >50 m. The data was collected while moving at 3-5 mph. Another example wherein different materials detected in a scene can be assigned different pseudo colors for easy discrimination between materials is illustrated by FIG. 16. Here disturbed earth, command wire, and foam are all detected and assigned different pseudo colors. Pixels containing AN were pseudo colored to indicate positive detection. The use of pseudo color enhancement is more fully described in U.S. patent Ser. No. 12/799,779, filed on Apr. 30, 2010, entitled "System and Method for Component Discrimination Enhancement based on Multispectral Addition Imaging," hereby incorporated by reference in its entirety.

In one embodiment, the system and method can be configured to utilize RGB video and CONDOR-ST SWIR HSI technology, available from ChemImage Corporation, Pittsburgh, Pa., in wide area surveillance and local area confirmation modes to operate while On-the-Move. In another embodiment, the system and method are configured so as to enable integration with LWIR, MM Wave, and/or GPR sensors via industry standard fusion software. In one embodiment, this fusion software may comprise ChemImage's FIST ("Forensic Integrated Search") technology, available from ChemImage Corporation, Pittsburgh, Pa. This technology is more fully described in pending U.S. patent application Ser. No. 11/450,138, filed on Jun. 9, 2006, entitled "Forensic Integrated Search Technology"; Ser. No. 12/017,445, filed on Jan. 22, 2008, entitled "Forensic Integrated Search Technology with Instrument Weight Factor Determination"; Ser. No. 12/196,921, filed on Aug. 22, 2008, entitled "Adaptive Method for Outlier Detection and Spectral Library. Augmentation"; and Ser. No. 12/339,805, filed on Dec. 19, 2008, entitled "Detection of Pathogenic Microorganisms Using Fused Sensor Data". Each of these applications are hereby incorporated by reference in their entireties.

The present disclosure also contemplates the incorporation of real-time anomaly detection and classification algorithms in a software package associated with the sensor. In such an embodiment, the system will have the ability to perform autonomous detection of a wide variety of targets. Such an embodiment provides for a single sensor system to support automated counter mine algorithms, aided target cuing, Aided Target Recognition (AiTR) of difficult targets, and anomaly detection and identification in complex/urban areas.

In another embodiment, the present disclosure provides for ChemFusion Improvements. Such improvements include the use of grid search methodology to establish improved weighting parameters for individual sensor modality classifiers under JFIST Bayesian architecture. Improvements in Pd and Pfa can be realized by full execution of combinatorial decision making applied to multiple detections afforded by hyperspectral imaging. In another embodiment, image weighted Bayesian fusion may be used.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method comprising:
   surveying a region of interest to generate a visible image;
   analyzing the visible image to identify one or more targets in the region of interest, wherein the one or more targets comprise at least one unknown material;
   illuminating the one or more targets to generate a plurality of interacted photons;
   passing the plurality of interacted photons through a liquid crystal tunable filter selected from the group consisting of a multi-conjugate liquid crystal tunable filter, an Evans split element liquid crystal tunable filter, a Solc liquid crystal tunable filter and a Fabry Perot liquid crystal tunable filter to generate a plurality of filtered photons comprising a plurality of wavelength bands;
   assessing the plurality of filtered photons using a spectroscopic imaging device to generate a SWIR hyperspectral image of the one or more targets; and
   analyzing the SWIR hyperspectral image by associating the at least one unknown material with a known material.

2. The method of claim 1, wherein the SWIR hyperspectral image comprises a digital image and a spatially resolved SWIR spectrum for each pixel in the image.

3. The method of claim 1, further comprising analyzing the SWIR hyperspectral image to identify the at least one unknown material.

4. The method of claim 3, wherein the analyzing further comprises comparing the SWIR hyperspectral image to a reference data base comprising at least one SWIR reference data set associated with a known material.

5. The method of claim 4, wherein the comparing comprises applying at least one chemometric technique.

6. The method of claim 1, wherein the one or more targets are identified based on at least one of size, shape, color, and combinations thereof.

7. The method of claim 1, wherein the surveying the region of interest comprises using a visible imaging device.

8. The method of claim 7, wherein the visible imaging device comprises an RGB camera.

9. The method of claim 1, wherein the plurality of interacted photons is selected from the group consisting of photons reflected by the target area, photons absorbed by the target area, photons scattered by the target area, photons emitted by the target area and combinations thereof.

10. The method of claim 1, wherein the at least one unknown material comprises one or more of an explosive material, a non-explosive material, a chemical material, an explosive residue, a material associated with an explosive material, a disturbed earth, a command wire, and combinations thereof.

11. The method of claim 1, further comprising applying a fusion algorithm to the visible image and the SWIR hyperspectral image.

12. The method of claim 1, further comprising obtaining one or more of a MWIR hyperspectral image of the one or more targets, a LWIR hyperspectral image of the one or more targets, and combinations thereof.

13. The method of claim 12, further comprising applying a fusion algorithm to a plurality of the visible images, the SWIR hyperspectral image, the MWIR hyperspectral image, and the LWIR hyperspectral image.

14. The method of claim 1, wherein surveying further comprises employing a telescope optic configured to focus on and locate the region of interest.

15. The method of claim 1, further comprising collecting the plurality of interacted photons with a telescope optic configured to increase the magnification of the region of interest.

16. The method of claim 1, further comprising generating one or more of a dynamic visible image of the one or more targets, a dynamic hyperspectral image of the one or more targets, and combinations thereof.

* * * * *